United States Patent [19]

Flynn et al.

[11] Patent Number: 5,095,110

[45] Date of Patent: Mar. 10, 1992

[54] PROCESS FOR THE PREPARATION OF SULFHYDRYL CONTAINING TRICYCLIC LACTAMS

[75] Inventors: Gary A. Flynn; Douglas W. Beight, both of Cincinnati, Ohio

[73] Assignee: Merrell Dow Pharmaceuticals Inc., Cincinnati, Ohio

[21] Appl. No.: 483,955

[22] Filed: Feb. 9, 1990

Related U.S. Application Data

[60] Continuation of Ser. No. 280,393, Dec. 5, 1988, abandoned, which is a division of Ser. No. 139,485, Dec. 30, 1987, abandoned.

[51] Int. Cl.$^5$ .......................................... C07D 223/14
[52] U.S. Cl. ................................... 540/522; 540/522
[58] Field of Search .......................................... 540/522

[56] References Cited

PUBLICATIONS

Noller, Textbook of Organic Chemistry, 3rd ed., W. B. Saunders Co., Philadelphia, 1966, p. 430.
McPhee, W. D. et al., Organic Syntheses Collective, vol. 3, 119-120 (1955).
Isler, O. et al., Helvetica Chimica Acta., 40 No. 139, 1242-1249 (1957).
Wiley, P. F. et al., J. Org. Chem., 41, No. 10, 1858-1862, (1976).

Primary Examiner—Mary C. Lee
Assistant Examiner—Joseph K. McKane
Attorney, Agent, or Firm—William J. Stein

[57] ABSTRACT

This invention relates to a process for preparing an olifinated tricyclic lactam which comprises reacting an amine with alkylnitrite to form a diazoamide compound which is further reacted with strong acid and phosphine, and finally with a strong base and formaldehyde.

8 Claims, No Drawings

PROCESS FOR THE PREPARATION OF SULFHYDRYL CONTAINING TRICYCLIC LACTAMS

This is a continuation, of application Ser. No. 208,393, filed Dec. 5, 1988, which is a divisional of application Ser. No. 139,485, filed Dec. 30, 1987, both now abandoned.

BACKGROUND OF THE INVENTION

A need exists for compounds which inhibit angiotensin converting enzyme (hereinafter ACE). The inhibition of ACE blocks the conversion of the decapeptide angiotensin I to angiotensin II. Angiotensin II is a potent pressor substance, therefore blood pressure lowering can result from inhibition of its biosynthesis, especially in animals and humans whose hypertension is angiotensin II related. Furthermore, ACE inhibition may also lower blood pressure by potentiation of bradykinin. Although the relative importance of these and other possible mechanisms remains to be established, ACE inhibitors are effective antihypertensive agents in a variety of animal models and are useful clinically in treating human patients with renovascular, malignant and essential hypertension. See, e.g., D. W. Cushman, et al., *Biochemistry*, 16, 5484 (1977).

Additionally, a need exists for compounds which are anti-ischemic agents useful in the treatment of reperfusion injury. Reperfusion injury is that injury which occurs when molecular oxygen is reintroduced into an ischemic tissue. An ischemic tissue is one that is deficient of blood due to a functional constriction or actual obstruction of a blood vessel. Ischemia (i.e., the deficiency of oxygenated blood in a tissue) can be caused by any means and in any tissue and includes ischemia to the heart or a portion of the heart resulting from a coronary thrombosis or any other blockage of the blood supply to the heart or a portion of the heart, ischemia surgically induced to the heart of a patient undergoing open-heart or coronary by-pass surgery, the ischemia which occurs to an organ or organ group such as a heart, heart-lung, liver, or kidney to be used in an organ transplant, ischemia occuring during circulatory shock, and ischemia which is caused by blockage of the arteries supplying the brain, i.e. stroke.

Likewise, a need exists for compounds that exert a strenghtening effect on the heart tissue of patients who have suffered heart failure. Heart failure, or cardiotonia, is the clinical condition resulting from the inablilty of the myocardium of the ventricles to maintain an adequate flow of blood to all the tissues of the body and includes backward heart-failure, congestive heart-failure, forward heart-failure, and left and right ventricular heart-failure. A cardiotonic agent is an agent which strenghtens the heart's action. The compounds effective in treatment of heart-failure function by strengthening the heart muscle by virtue of their ability to enhance myocardial contractile force and by reducing work load by virtue of their vasodilator activity.

DESCRIPTION OF THE INVENTION

This invention relates to certain conformationally rigid sulfhydryl containing fused tricyclic lactams of the formula

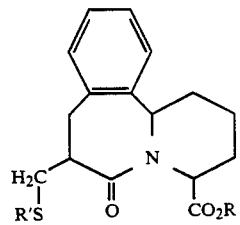

wherein

R is hydrogen, $C_1$–$C_6$ lower alkyl, or ($C_6$–$C_{12}$)aryl($C_1$–$C_6$)lower alkyl; and R' is hydrogen or —COR, wherein R is as defined above, and to the pharmaceutically-acceptable salts thereof. The invention also concerns the intermediates and processes useful for their preparation, and to their pharmacological effect and use in the treatment of hypertension (i.e. to inhibit angiotensin converting enzyme), ischemia (i.e. to treat injury occurring during the reperfusion of ischemic tissue), and cardiotonia (i.e. to enhance myocardial contractile force and to treat heart failure).

As used herein, the term "$C_1$–$C_6$ lower alkyl" and the "$C_1$–$C_6$ lower alkyl" portion of the aryl groups means straight or branched chain alkyl groups having from one to six carbon atoms and includes such groups as methyl, ethyl, n-propyl, isopropyl, n-butyl, isobutyl, sec-butyl, tert-butyl, and the like, as well as vinyl, propargyl, butenyl, and the like. The term "$C_6$–$C_{12}$ aryl" refers to aryl groups containing six to twelve carbon atoms and includes such groups as phenyl, naphthyl, indenyl, biphenyl and benzofused cycloalkyl groups such as, for example, indanyl and 1,2,3,4,-tetrahydronaphthyl. Illustrative examples of the compounds of this invention include:

[4S-(4 alpha,7 alpha,12b beta)]-1,2,3,4,6,7,8,12b-octahydro-7-(mercaptomethyl)-6-oxo-pyrido[2,1-a][2]benzazepine-4-carboxylic acid

[4S-(4 alpha,7 alpha,12b beta)]-1,2,3,4,6,7,8,12b-octahydro-7-[(acetylthio)methyl]-6-oxo-pyrido[2,1-a][2]benzazepine-4-carboxylic acid

[4S-(4 alpha,7 alpha,12b beta)]-1,2,3,4,6,7,8,12b-octahydro-7-[(benzoylthio)methyl]-6-oxo-pyrido[2,1-a][2]benzazepine-4-carboxylic acid

[4S-(4 alpha,7 alpha,12b beta)]-1,2,3,4,6,7,8,12b-octahydro-7-(mercaptomethyl)-6-oxo-pyrido[2,1-a][2]benzazepine-4-carboxylic acid methyl ester

[4S-(4 alpha,7 alpha,12b beta)]-1,2,3,4,6,7,8,12b-octahydro-7-(mercaptomethyl)-6-oxo-pyrido[2,1-a][2]benzazepine-4-carboxylic acid diphenylmethyl ester

[4S-(4 alpha,7 alpha,12b beta)]-1,2,3,4,6,7,8,12b-octahydro-7-[(benzoylthio)methyl]-6-oxo-pyrido[2,1-a][2]benzazepine-4-carboxylic acid methyl ester

[4S-(4 alpha,7 alpha,12b beta)]-1,2,3,4,6,7,8,12b-octahydro-7-[(benzoylthio)methyl]-6-oxo-pyrido[2,1-a][2]benzazepine-4-carboxylic acid diphenylmethyl ester.

As is true for most classes of therapeutically effective compounds, certain subclasses and certain species which are especially effective are preferred over others. In this instance, those compounds of Formula I wherein R and R' are both hydrogen are preferred.

Also preferred are those compounds having the diastereomeric configuration represented by the structure:

All enantiomeric isomers and diastereomeric isomers and mixtures thereof of the compounds of Formula I are encompassed within the scope of this invention. The separation of said isomericmixtures can be accomplished by standard techniques known in the art.

The tricyclic lactams of this invention can readily be prepared by the reactions depicted in Reaction Scheme I:

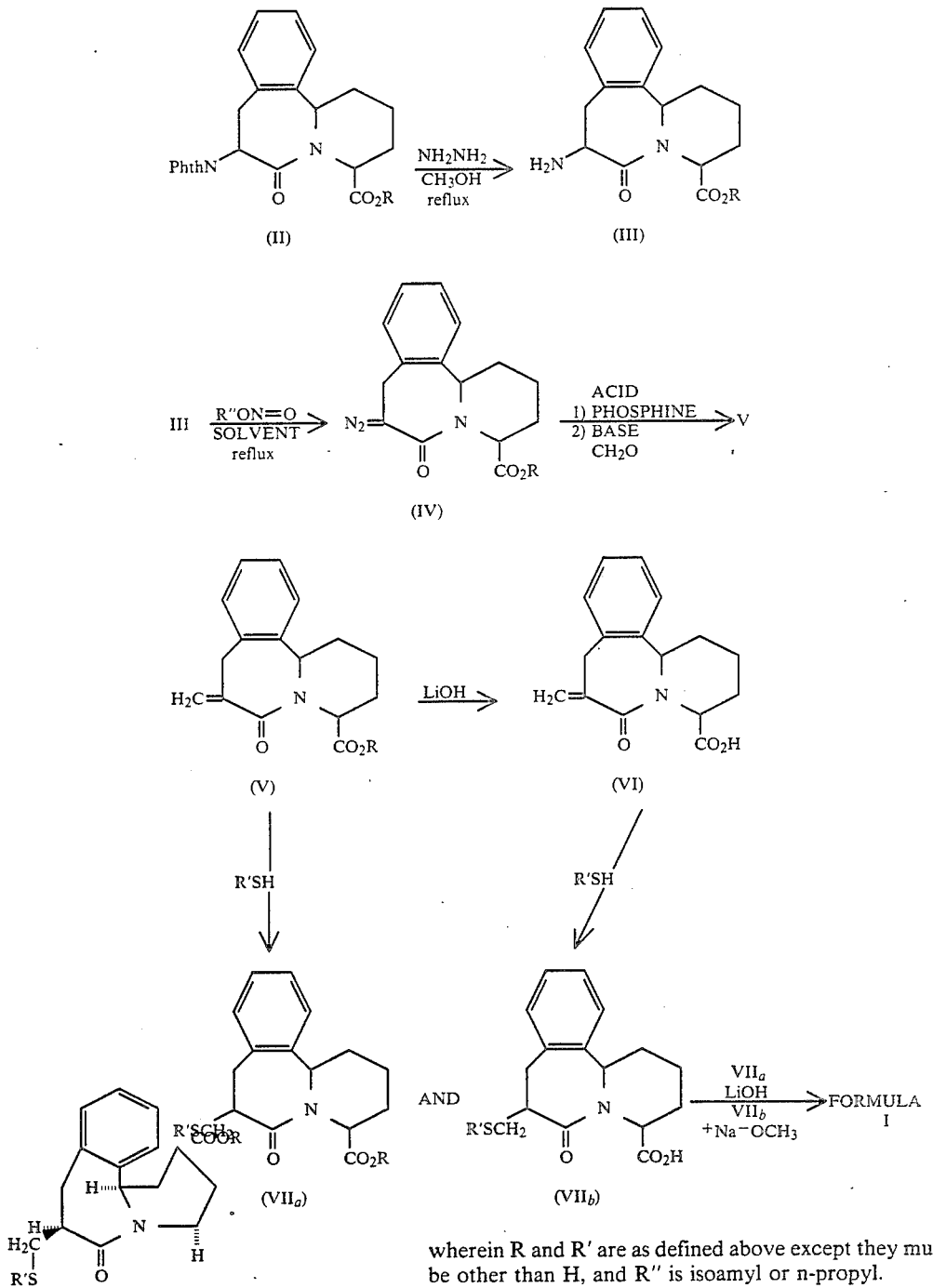

wherein R, and R' are as defined in Formula I and wherein the steriochemistry is 4(S), 7(S), and 12b(R), the preferred R, and R' groups being as described above.

wherein R and R' are as defined above except they must be other than H, and R" is isoamyl or n-propyl.

In essence, Reaction Scheme I illustrates that the tricyclic lactams of Formula I can be prepared by converting the phthalamide starting material II (whererin "Phth" is a nitrogen protecting phthalimide group), to the amine III by reacting it with excess hydrazine hydrate (NH$_2$NH$_2$) in an appropriate organic solvent such as methanol (CH$_3$OH) under nitrogen and under reflux conditions The resulting amine III is then treated with an equivalent amount of alkylnitrite (R"ON=O) such as isoamylnitrite or propyl nitrite, in the presence of acetic acid and an inert solvent such as dichloromethane or chloroform under nitrogen and under reflux conditions to produce the diazoamide intermediate IV. The diazo compound IV is first reacted with a mixture of two equivalents of a strong acid such as methanesulfonic acid or trifluoromethanesulfonic acid and an excess of a phosphine such as triphenylphosphine or tributylphosphine under nitrogen, at a temperature of from about $-70°$ C. to about $50°$ C., preferably at about $-40°$ C. to about $-20°$ C., and the resulting mixture subsequently reacted with two equivalents of a strong base, such as potassium carbonate, and excess formaldehyde (CH$_2$O) to yield the olefinated lactam V. The olefinic lactam (V) can be coupled with an appropriate thioester (R'SH) by means of a Michael reaction using a base to yield the thioester VII$_a$, and then subjected to lithium hydroxide (LiOH) saponification to yield the compounds of Formula I (where the product containing R as hydrogen, or R as other than hydrogen is dependent on the duration of the reaction). Or alternatively, V can be hydrolyzed with lithium hydroxide (LiOH), when R is other than hydrogen, to produce the olefinic acid VI. VI can then be coupled with an appropriate thioester (R'SH) by means of a Michael reaction using a base to produce the thioester VII$_b$, which, in a suitable deoxygenated solvent such as methanol, can be subjected to sodium methoxide ($^+$Na$^-$OCH$_3$) cleavage, yielding the sulfur containing tricyclic lactams of Formula I.

The intermediate compounds of Formulas IV and V are useful in the synthesis of the compounds of Formula I.

Preparation of the starting material (II) is illustrated by Reaction Scheme II below. In preparation of the methyl ester (II), it is generally preferred to initiate the sequence of reaction steps by utilizing N-protected phenylalanine which, when converted to its acid chloride (VIII, wherein Phth is a nitrogen protecting phthalamide group), is coupled by treatment with an aminovinyl chloride (IX$_a$) or an -OH protected vinyl amino acid (IX$_b$) according to the well-known Schott-Baumann reaction In this reaction, the reactants are coupled in the presence of sodium carbonate/acetone and water, preferably at room temperature and then subjected to an acidification step to produce intermediate compounds (X$_a$ and X$_b$). These intermediates are treated with ozone (O$_3$) in methylene chloride containing an alcohol such as methanol (CH$_3$OH) at $-78°$ C., quenched with dimethylsulfide (Me$_2$S) and pyridine, and the isolated products treated with trifluoroacetic acid/methylene chloride (H$^+$) at reflux temperatures to produce further intermediates (XI$_a$ and XI$_b$). These subsequent intermediates are then treated with trifluoromethanesulfonic acid (CF$_3$SO$_3$H) according to the well-known Friedel-Crafts cyclization procedure to produce the compound of Formula II:

Reaction Scheme II

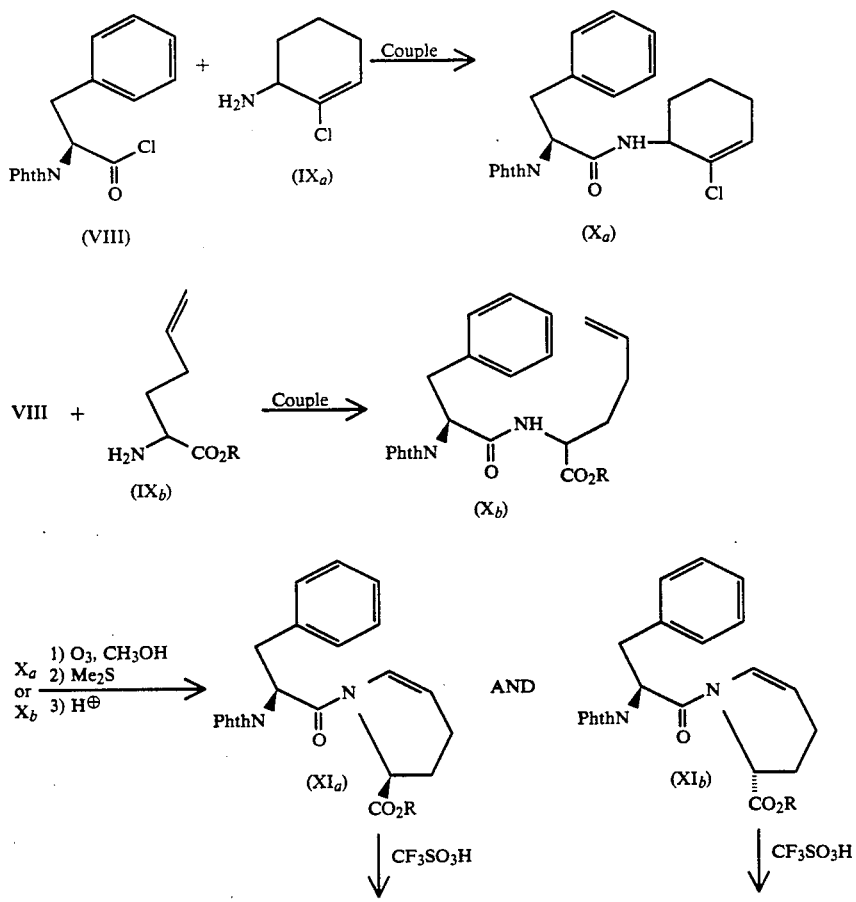

-continued
Reaction Scheme II

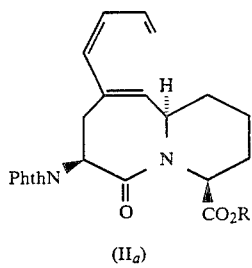

(IIa)

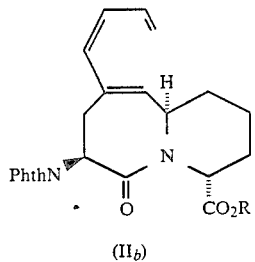

(IIb)

wherein R is as defined above.

The following specific examples are presented to illustrate the synthesis of the compounds of this invention, but they should not be construed as limiting the scope of this invention in any way.

EXAMPLE 1

[2(S)]N-(2-Chloro-2-Cyclohexene-1-yl)-1,3-Dihydro-1,3-Dioxo-2H-Isoindole-2-(S)-(Phenylmethyl-2-Acetamide ($X_a$)

Step A. 2-(2-Chloro-2-Cyclohexen-1-yl)-1H-Isoindole-1,3(2H)-Dione

A solution of 11.0g (72.8 mmol) 1,6-dichlorocyclohexene, 20.0g (108 mmol) potassium phthalimide and 1.0 g (6.0 mmol) potassium iodide in 50 ml dry dimethylformamide was stirred 24 hours at 110° C. under an atmosphere of nitrogen. The reaction mixture was allowed to cool then poured into 30 ml diethyl ether. The dark mixture was filtered, then the ether and DMF removed in vacuo. The dark crystalline residue was dissolved in ethyl acetate then chromatographed on 500 g flash silica eluting with 10% to 20% ethyl acetate/hexane. Concentration of appropriate fractions followed by recrystallization from ethyl acetate/hexane gave 14.0 g (73.5%) of the desired phthalimide, mp 99°-103° C.

Step B. A solution of 6.0 g (120 mmol) of hydrazinehydrate and 26.1 g (100 mmol) of N-phthalimido-6-amino-1-chlorocyclohexene in 150 ml methanol was refluxed under $N_2$ for 3 hrs., cooled to 25° C. and allowed to stir for 3 hrs. The mixture was filtered, concentrated, poured into 300 ml 1N HCl, and washed with 200 ml $CH_2Cl_2$. The aqueous layer was basified and extracted with three 500 ml portions of $CH_2Cl_2$. The organics were dried over $MgSO_4$, filtered, and concentrated to give 9.25 g (70 mmol) of crude amine. The neutral extract was concentrated to give 6.0 g of unreacted starting phthalimide. To a stirred solution of 21 g (71 mmol) of phthalimido-L-phenylalanine and 18.5 g (75 mmol) of N-carbethoxy-2-ethoxy-1,2-dihydroquinoline in 200 ml $CH_2Cl_2$ at 25° C. under $N_2$ was added 9.25 g (70 mmol) of the 6-amino-1-chlorocyclohexene in 20 ml $CH_2Cl_2$ over 30 min. After stirring for 18 hours, the reaction mixture was washed with two 200 ml portions of 10% HCl solution, 200 ml sat. $NaHCO_3$ solution, and brine. The organics were dried over $MgSO_4$, filtered and concentrated to give a solid. Recrystallization from $CH_2Cl_2$/ hexane gave 26.1 g of a mixture of the desired 2-(S) diastereomeric amides ($X_a$) which were not separated at this point. (64% overall yield): IR(KBr) 3400, 1775, 1715, 1650, 1530, 1380, $cm^{-1}$; $^1H$ NMR $\delta 1.60$ (m,2H), 1.82 (m,2H), 2.05 (m,2H), 3.49 (s,1H), 3.59 (s,1H), 4.60 (m, 1H), 5.05 (dd, 1/2H, $J_a=10H_z$, $J_b=2H_z$), 5.17 (dd, 1/2H, $J_a=10H_z$, $J_b=2H_z$), 5.95 (t, 1H, J=7 $H_z$), 6.45 (m,1H), 7.10 (s,5H), 7.70 (m,4H).

Anal. Calcd. for $C_{23}H_{21}ClN_2O_3$: C,67.56; H,5.18; N,6.85. Found: C,67.40; H,5.30; N,6.80.

EXAMPLE 2

[S(R*,R*)]-I-2-(1,3-Dihydro-1,3-Dioxo-2H-Isoindol-2-yl)-1-Oxo-3-Phenylcropyl]-1,2,3,4-Tetrahydro-2-PyridineCarboxylicacid, Methyl Ester (XIa)

A solution of 12.2 g (30 mmol) of the vinyl chloride from Example 1 in 300 ml $CH_2Cl_2$ containing 20 ml absolute methanol was cooled to $-70°$ C. and stirred while a stream of ozone in oxygen (generated by a Welsbach Ozonator) was passed into the solution via a glass frit. When the solution turned blue, excess ozone was removed by passing dry $N_2$ into the solution. The reaction mixture was treated with 20 ml methyl sulfide and 4 ml pyridine, then allowed to gradually warm to 25° C. and stir for 20 hours. The solution was poured into 200 ml 10% HCl solution and the organics were separated, washed well with $H_2O$, dried over $MgSO_4$ and concentrated to give 13.0 g of an amber oil. The crude ozonolysis product was dissolved in 200 ml $CH_2Cl_2$ containing 0.5 ml trifluoroacetic acid and refluxed under $N_2$ for 3 hours. The cooled solution was washed with saturated $NaHCO_3$ solution, dried over $MgSO_4$ and concentrated to give 12.2 g of an amber oil. Preparative HPLC separation using 50% ethyl acteate/hexane (Waters Prep-500 one recycle) gave 4.3 g (10.1 mmol) of each diastereomeric acylenamine XIa and XIb, (68% overall yield). Isomer XIa was recrystallized from $CH_2Cl_2$/ hexane to give a fine white crystalline powder: mp 146°-147° C.; $[\alpha]^{Amb}=-320.1°$ (c=1.1,$CHCl_3$); IR (KBr) 1770, 1740, 1720, 1670, 1650, 1390, 1220, 722 $cm^{-1}$; $^1H$ NMR $\delta 1.85$ (m,2H), 2.30 (m,2H), 3.50 (d, 2H, J=7 $H_z$), 3.72 (s,3H), 4.71 (m,1H), 5.20 (m,1H), 5.27 (t, 1H, J=7 $H_z$), 6.45 (d, 1H, J=9 $H_z$), 7.12 (s,5H), 7.71 (m,4H).

Anal. Calcd. for $C_{23}C_{22}N_2O_5$: C,68.89; H,5.30; N,6.69. Found C,68.61; H,5.26; N,6.56.

EXAMPLE 3

]4S-($4\alpha,7\alpha,12b\beta$)]-7-(1,3-Dihydro-1,3-Dioxo-2H-Isoindo-2-yl)-1,2,3,4,-6,7,8,12b-Octahydro-6-Oxopyrido[2,1-a][2]Benzazepine-4-Carboxylic Acid, Diphenylmethyl Ester (IIa)

To a stirred solution of 4.20 g (10.0 mmol) of desired acylenamine from Example 2 in 20 ml $CH_2Cl_2$ under $N_2$ atmosphere was added 6 ml $CF_3SO_3H$. After stirring at 20° C. for 18 hours, the solution was poured onto ice and extracted into 200 ml ethyl acetate. The organics were washed well with water, dried over $MgSO_4$ and concentrated. The residue was dissolved in $CH_2Cl_2$ and treated with 2.2 g diazodiphenylmethane and allowed to stand for 12 hours. The solution was concentrated and the residue was flash chromatographed on 400 ml silica using 33% ethyl acetate/hexane to give 4.5 g (7.7 mmol, 77% yield) of the title benzhydrylester (R=CHPh$_2$) as a foam. Recrystallization from CH$_2$Cl$_2$/hexane was slow but gave 4.3 g (75% yield) of pure transparent plates: mp. 156°–157° C.; $[\alpha]^{Amb} = -87.6°$ C. (c=0.6, CHCl$_3$);IR 1780, 1717, 1643, 1450, 1379 cm$^{-1}$; 'H NMR δ1.8–2.1 (m,4H), 2.38 (m,2H); 3.23 (dd, 1H, $J_a=18$ Hz, $J_b=16$ Hz) 4.38 (dd, 1H, $J_a=19$ Hz, $J_b=12$ Hz), 5.30 (dd, 1H, $J_a=6$ Hz, $J_b=2$ Hz), 5.42 (dd, 1H, $J_a=6$ Hz, $J_b=4$ Hz, 6.05 (dd, 1H, $J_a=12$ Hz, $J_b=6$ Hz), 6.30 (s,1H), 6.61 (d, 1H, $J=7$ Hz), 6.9–7.4 (m,13 H), 7.75 (m,2H), 7.92 (m,2H).

Anal. Calcd. for C$_{36}$H$_{30}$N$_2$O$_5$: C,75.77; H,5.30; N,4.91. Found: C,75.79; H,5.46; N,4.77.

EXAMPLE 4

[4S-(4α,7α,12bβ)]-7-(1,3-Dihydro-1,3-Dioxo-2H-Isoindol-2-yl)-1,2,3,4,6,7,8,-12b-Octahydro-6-Oxopyrido[1-a][2]Benzazepine-4-Carboxylic Acid, Methyl Ester (IIb)

Alternatively the cyclization product could be treated with diazomethane to give the methyl ester from Example 3 (R=CH$_3$): mp 138°–149° C. $[\alpha]^{Amb} = -122.4°$ (c=0.97,EtOH); IR 71778, 1720, 1655, 1620, 1375 cm$^{-1}$,'H NMR δ1.7–2.2 (m,4H), 2.43 (m,2H), 3.10 (s,3H), 3.44 (dd, 1H, $J_a=17$ Hz, $J_b=6$ Hz), 4.42 (dd, 1H, $J_a=17$ Hz, $J_b=12$ Hz), 5.23 (dd, 1H, $J_a=6$ Hz, $J_b=2$ Hz), 5.47 (dd, 1H, $J_a=6$ Hz, $J_b=4$ Hz), 6.08 (dd, 1H, $J_a=12$ Hz, $J_b=6$ Hz), 7.23 (m,4H), 7.77 (m,2H), 7.89 (m,2H).

Anal. Cacd. for C$_{24}$H$_{22}$N$_2$O$_5$: C,68.89; H,5.30; N,6.69. Found: C,68.98; H,5.83; N,6.63.

EXAMPLE 5

[4S-(4α,7α,12bβ)]-7-Amino-1,2,3,4,6,7,8,12b-Octahydro-6-Oxo-Pyrido[2,1-a][2]Benzazepine-4-Carboxylic Acid Methyl Ester (III)

Twenty ml (20 mmol) 1M hydrazine hydrate in methanol was added to a mixture of 4.18 g (10.0 mmol) methyl ester of Example 4 in 30 ml methanol. The mixture was allowed to stir at ambient temperature under an atmosphere of nitrogen for 18 hr. The mixture was then filtered through Celite, washed thoroughly with methanol, and concentrated The resulting oil was partitioned between methylene chloride and water, and the methylene chloride portion was washed with an additional 20 ml of water. The solution was dried over anhydrous magnesium sulfate, filtered and concentrated in vacuo to yield 3.05 g (106%) of the title ester. The product was recrystallized from methylene chloride/hexane to give analytically pure amine as a partial hydrate.

'H NMR (CDCl$_3$): 7.15 (m, 4H); 5.46 (m, 1H); 5.34 (m, 1H) 4.69 (dd, $J_a=11$Hz, $J_b=5$Hz, 1H); 2.98 (S, 3H); 2.94 (dd, $J_a=17$Hz, $J_b=14$Hz); 2.43 (m,2H); 2.08–1.70 )complex, 1.82 (s, 2H). Calc. for C$_{16}$H$_{20}$N$_2$O$_3$.0.3 H$_2$O: C,65.42; H,6.45; N,9.54: Found: C,65.39: H,7.18: N, 9.58.

EXAMPLE 6

4S-trans-1,2,3,4,6,7,8,12b-Octahydro-7-Methylene-6-Oxo-Pyrido[2,1-a][2]Benzazepine-4-Carboxylic Acid Methyl Ester (V)

Isoamyl nitrite (1.13 g, 4.8mmol) was added to a solution of 1.17 g (4.0 mmol) of the title ester of Example 5 and 44 microliters (0.8 mmol) of acetic acid in 20 ml of dry dichloromethane. The solution was refluxed under nitrogen for 85 min. and allowed to cool. The solution was extracted once with 20 ml of 5% aqueous sulfuric acid, washed with water, and shaken with 20 ml saturated sodium bicarbonate (NaHCO$_3$) solution. The acidic extract was made basic and back extracted with ethyl acetate to recover approximately 300 mg unreacted starting amine. The dichloromethane fraction was dried over sodium sulfate (Na$_2$SO$_4$) and concentrated to give 616 mg of 4S-trans-7-diazo-1,2,3,4,6,7,8,12b-octahydro-6-oxo-pyrido[2,1-a][2]benzazepine-4-carboxylic acid methyl ester (IV) (51.4% yield). The diazo compound (616 mg, 2.1 mmol) was dissolved in 10 ml methylene chloride (CH$_2$Cl$_2$) and added dropwise over 13 min. to a stirred solution of 2.16 g (8.23 mmol) of triphenylphosphine and 0.33 ml (4.1 mmol) of trifluoromethanesulfonic acid at −40° C. under an atmosphere of nitrogen. Stirring was continued for 2.5 hr at −20° C. The solution was concentrated in vacuo and the resulting oil was dissolved in 25 ml 95% ethyl alcohol. To this stirred solution was added a solution of 0.59 g (4.2 mmol) of potassium carbonate (K$_2$CO$_3$) in 6 ml water followed immediately by 4 ml of 37% formaldehyde solution. After stirring for 23 min. at 25 ° C., the reaction mixture was quenched with 4 ml 1N HCl, filtered, and the solid washed with 10 ml 50% alcohol/water. The filtrate was concentrated in vacuo, the residue dissolved in ethyl acetate, and dried over MgSO$_4$ and concentrated *in vacuo*.

Flash chromatography on silica gel using 40% ethyl acetate in hexane afforded 197mg (17.3% overall yield) of the title compound.

'H NMR δ(CDCl$_3$): 7.1–7.3 (m, 4H); 5.70 (s, 1H); 5.42 (s, 1H); 5.3–5.4 (m, 2H); 4.02 (d, J=20 Hz, 1H); 3.95 (d, J=20 Hz, 1H); 3.05 (s, 3H); 2.3–2.5 (m, 2H); 1.6–2.1 (m, 4H).

EXAMPLE 7

4S-trans-1,2,3,4,6,7,8,12b-Octahydro-7-Methylene-6-Oxo-Pyrido[2,1-a][2]Benzazepine-4-Carboxylic Acid (VI)

One molar lithium hydroxide (0.22 ml, 0.22 mmol) was added to a solution of 32 mg (0.11 mmol) of the title compound of Example 6 in 1 ml methanol. The solution was allowed to stir at ambient temperature under an atmosphere of nitrogen for 20 hr. The mixture was then diluted with 10 ml water, and extracted once with 10 ml ethyl acetate. The resulting aqueous solution was acidified with 1N HCl, then extracted with three portions of 7 ml methylene chloride. The methylene chloride portions were combined, dried over anhydrous magnesium sulfate, then concentrated in vacuo to yield 20 mg (66%) of the title compound.

'H NMR δ(CDCl$_3$) 7.40–7.10 (complex, 4H); 5.75 (s, 1H); 5.45 (s, 1H); 5.30 (t, 5=3 Hz, 1H); 5.20 (dd, $J_a=4$ Hz, $J_b=2$ Hz); 3.98 (d, J=15 Hz, 1H); 3.85 (d, J=15 Hz, 1H); 2.5–2.3 (complex, 2H); 2.0–1.7 (complex, 4H); $^{13}$C NMR δ(CDCl$_3$); 17.77, 17.94, 24.43, 25.18, 38.11, 50.84, 52.40, 120.12, 124.73, 126.09, 127.90, 129.32, 137.03, 138.03, 142.74, 171.34, 174.45.

EXAMPLE 8

[4S-(4α,7α,12bβ)]-7-[(benzoylthio)methyl]-1,2,3,4,6,7,8,12b-Octahydro-6-Oxo-Pyrido[2,1-a][2]Benzazepine-4-Carboxylic Acid (VIIb)

Thiolbenzoic acid (59 mg, 0.42 mmol) and 65 microliters (0.47 mmol) triethylamine were added to a solution of 115 mg (0.42 mmol) of the title compound of Example 7 in 7 ml methanol at ambient temperature under an atmosphere of nitrogen. After stirring 24 hr., while the reaction was still incomplete, the solution was concentrated to 1 ml, then an additional 60 microliters (0.43) triethylamine and 7 drops thiolbenzoic acid were added. After stirring an additional 24 hr., the reaction was quenched with excess 1N HCl then extracted into ethyl acetate. The ethyl acetate solution was washed once with brine, dried over anhydrous magnesium sulfate and concentrated in vacuo. Some thiolbenzoic acid was removed by Kugelrohr distillation (60 °C./0.7 torr). The residue was allowed to cool yielding 190 mg (110%) of the crude title compound. The compound was purified by HPLC (7.5 mm×250 mm 10 micron μ-porosil column; 0.5% acetic acid, 5% isopropanol, 94.5% hexane as eluant; 4 ml per min. flow rate), to yield 35 mg of the title compound (20%).

NMR δ(CDCl$_3$): 8.00 (d, J=7 Hz, 2H); 7.60 (m, 1H); 7.45 (m, 2H)); 7.25–7.05 (complex m, 4H); 5.55 (m, 1H); 5.25 (m, 1H); 3.90 (m, 1H); 3.50–3.35 (complex m, 3H); 2.95 (dd, J$_a$=17 Hz, J$_b$=13 Hz, 1H); 2.50 (complex d, J =10 Hz, 1H); 2.35 (complex d, J =10 Hz, 1H); 2.00 (complex m, 2H); 1.80 (complex m, 2H).

The following compound can be prepared by substituting thiolacetic acid for thiolbenzoic acid above, and following the procedure of Example 8: [4S-(4α,7α,12bβ)]-1,2,3,4,6,7,8,12b-octahydro-7-[(acetylthio)methyl]-6-oxo-pyrido[2,1-a][2]benzazepine-4-carboxylic acid.

The following compound can be prepared by substituting the unsaturated methyl ester title compound of Example 5 for the title compound of Example 7 and following the procedure of Example 8: [4S-(4α,7α,12bβ)]-1,2,3,4,6,-7,8,12b-octahydro-7-[(benzoylthio)methyl]-6-oxo-pyrido-[2,1-a][2]benzazepine-4-carboxylic acid methyl ester.

Further treatment of the product just named above with an excess of sodium methoxide in degassed methyl alcohol for a short period of time under an atmosphere of nitrogen, and isolation by chromatography yields: [4S-(4α,7α,12bβ)]-1,2,3,4,6,7,8,12b-octahydro-7-(mercaptomethyl)-6-oxo-pyrido[2,1-a][2]benzazepine-4-carboxylic acid methyl ester.

The following compound can be prepared by treating the title compound of Example 8 with diazodiphenylmethane and isolating by chromatography: [4S-(4α,7α,12bβ)]-1,2,3,4,6,7,8,12b-octahydro-7-[(benzoylthio)methyl]-6-oxo-pyrido[2,1-a][2]benzazepine-4-carboxylic acid diphenylmethyl ester.

Further treatment of the product just named above with an excess of sodium methoxide in degassed methyl alcohol for a short period of time under an atmosphere of nitrogen, and isolation by chromatography yields: [4S-(4α,7α,12bβ)]-1,2,3,4,6,7,8,12b-octahydro-7-(mercaptomethyl)-6-oxo-pyrido[2,1-a][2]benzazepine-4-carboxylic acid diphenylmethyl ester.

EXAMPLE 9

[4S-(4α,7α,12bβ)]-1,2,3,4,6,7,8,12b-Octahydro-7-(mercaptomethyl)-6-Oxo-Pyrido[2,1-a][2]Benzazepine-4-Carboxylic Acid (VII$_a$)

One molar sodium methoxide (350 microliters) was added to a solution of 27 mg (66 micromoles) of the title compound of Example 6 in 7 ml methanol deoxygenated with argon at ambient temperature under an atmosphere of argon. After stirring for 2 hr., the solution was made acidic with excess 1N HCl, saturated with sodium chloride, then extracted into ethyl acetate. The ethyl acetate solution was concentrated in vacuo yielding the title compound, which purified by HPLC (7.5 mm×250 mm 10 micron μ-Porisil column; 0 5% acetic acid, 5% isopropanol, 94.5% hexane as eluant; 4 ml per min. flow rate). The yield of the purified title compound was 10 mg (50%).

$^1$H NMR δ(CDCl$_3$): 7.25–7.00 (m, 4H); 5.55 (m, 1H); 5.20 (m, 1H); 5.75 (m, 1H); 3.30 (dd, Ja=18 Hz, Jb=8 Hz, 1H); 3.10 (dt, Jd =13 Hz, Jt =8 Hz, 1H); 2.85 (dd, Ja=14 Hz, Jb=Jb=18 Hz, 1H); 2.50 (complex m, 2H); 2.35 (broad d, J =10 Hz, 1H); 2.05–1.90 (complex, 2H); 1.85 (dd, Ja=8 Hz, Jb=10 Hz, 1H); 1.80–1.65 (complex, 2N). $^{13}$C NMR δ (CDCl$_3$): 175.26, 173.42, 136.90, 136.28, 130.68, 127.61, 125.71, 125.06, 50.92, 50.59, 44.78, 35.77, 26.50, 25.15, 25.11, 16.97.

The compounds of this invention are useful both in the free carboxylate form and as salts. The expression "pharmaceutically-acceptable salt" means any organic or inorganic addition salt of the carboxylate compounds of Formula I. These salts are included within the scope of this invention. Such salts include ammonium salts; alkali metal salts, such as sodium and potassium salts; alkaline earth metal salts, such as the calcium and magnesium salts; salts with organic bases such as, for instance, dicyclohexylamine salts, N-methyl-D-glucamine, and salts with amino acids such as arginine and lysine; and the like. The non-toxic, physiologically acceptable salts are preferred, although other salts are also useful, for, for example, isolating or purifying the product.

The salts can be formed by conventional means such as by reacting the free acid forms of the product with one or more equivalents of the appropriate base in a solvent or medium in which the salt is insoluble, or in a solvent such as water which is then removed in vacuo or by freeze-drying, or by exchanging the cations of an existing salt for another cation on a suitable ion exchange resin.

The utility of the compounds of this invention as antihypertensive agents can be determined by the evaluation of ACE inhibition in in vitro enzyme inhibition assays. For example, a useful method of evaluation is that of Y. Piquilloud, A. Reinharz and M. Roth, *Biochem. Biophys. Acta,* 206, N$_{36}$ (1970), in which the hydrolysis of cardobenzyloxyphenylalanylhistidinyl-leucine is measured. In vivo evaluations may be made, for example, in normotensive rats challenged with angiotensin I by the technique of J. R. Weeks and J. A. Jones, *Proc. Spc. Exp. Biol. Med.,* 104, 646 (1960), or in a high renin rat model such as that of S. Koletsky, et al., *Proc. Soc. Exp. Biol. Med.,* 125, 96 (1967).

The following Table indicates the activity of a compound of this invention as an ACE inhibitor as determined by a standard and well known procedure for assaying the enzyme-enhanced conversion of a substrate into product as an indication of enzyme activity. This procedure utilizes a continuous, spectrophotometric method for following the pre-equilibrium interaction of ACE with the substrate/product complex as set forth by Holmquist, et al, in *Analytical Biochemisty*, 95, (1979) 540-548. Substrate, 1 mM 2-furanacryloyl-L-Phe-Gly-Gly, and inhibitor, at the indicated concentration, were thermally equilibrated in 2 ml of buffer to 25° C. in the chamber of a Cary 210 spectrophotometer, then rabbit lung ACE was added to complete the assay mixture, and the reaction monitored and recorded by computer. Captopril, a known ACE inhibitor, was used as a positive control for the assay. The significantly reduced amount of product formed when the reaction is run in the presence of the compound of this invention demonstrates the compound's usefulness as an ACE inhibitor as illustrated in Table I.

TABLE I

| Concentration of inhibitor | Time | Concentration of end product |
|---|---|---|
| Captopril, 10 nM (positive control) | 8 min. | 160 nM |
| Compound 1*, 10 nM | 8 min. | 95 nM |
| Compound 1*, 5 nM | 8 min. | 148 nM |

*Compound 1 is [4S-(4 alpha,7 alpha,12b beta)]-1,2,3,4,6,7,8,12b-octahydro-7-(mercaptomethyl)-6-oxo-pyrido[2,1-a][2]benzazepine-4-carboxylic acid; i.e. where R and R' are both hydrogen.

The amount of the active ingredient to be administered to a patient for the treatment of hypertension can vary widely according to such considerations as the particular dosage unit employed, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 30 mg/kg. A unit dosage may contain from 25 to 525 mg of active ingredient, and can be taken one or more times per day. The compound of Formula I can be administered with a pharmaceutical carrier using conventional dosage unit forms either orally, parenterally, topically, or the like, as described below.

The compounds of this invention can be administered as the sole anti-hypertensive agent or in combination with other anti-hypertensives and/or diuretics and/or calcium entry blockers. For example, the compounds of this invention can be given in combination with such compounds as benzthiazide, clonidine, deserpidine, furosemide, hydralazine hydrochloride, indacrinone and variable ratios of its enantiomers, prazosin, propanolol, reserpine, and the like, as well as admixtures and combinations thereof.

Typically, the individual daily dosages for these combinations can range from about one fifth of the minimally recommended clinical dosages to the maximum recommended levels for the entities when they are given singly.

The ability of the compounds of this invention to reduce reperfusion injury can be demonstrated by their ability reduce myocardial stunning. Myocardial stunning is the prolonged loss of contractile function in the absence of necrosis following short periods of myocardial ischemia. (See, E. Braunwald and R. A. Kloner, Circ. 66, 1146-1149 (1982). Stunning has been implicated in a variety of disorders and conditions in which blood circulation has been temporarily cut off from the heart or in which a relatively high concentration of oxygen derived free radicals is known to be present.

In order to measure stunning, an anesthetized dog is instrumented to record blood pressure, heart rate electrocardiogram (ECG), cardiac contractile force, and left intraventricular systolic pressure and its derivative. Two crystal sets each with two crystals are implanted in the left myocardium to measure shortening of the myocardial segments between the crystals of each set. One set is placed toward the base and the other toward the apex. The apical crystal set is placed to be within the ischemic area during occlusion of the left anterior descending coronary artery (LAD) at the intermediate point. The basal set of crystals are placed to be in the normal myocardium during ischemia. Following a control period, the LAD is occluded for 15 minutes followed by 3 hours of reperfusion. A short period of occlusion is used to prevent any substantial necrosis. During the period of occlusion, the shortening of the myocardial segment between the apical crystals (ischemic myocardium) decreases and actually shows a lengthening during contraction in control dogs whereas the shortening between the basal crystals (nonischemic myocardium) is maintained. When the occlusion period is ended and reperfusion of the ischemic myocardium has commenced, contractility of the previously ischemic area improves but does not recover during the 3 hour reperfusion period. This disparity in contractility (reported as per cent shortening) between the normal and previously ischemic region is referred to as stunning and is reported below in Table 1. To avoid any possible effect on stunning by the positive inotropic activity of the compound of this invention, the positive inotropic effect of the compound was allowed to dissipate at least 80% prior to occlusion of the LAD.

For use in the treatment of reperfusion injury (ischemia), the compound of Formula I will ideally be administered to the patient at the time of tissue reperfusion and treatment therewith will continue until such time that reperfusion injury of the type being treated has normally ceased, which will typically be for about 2 to 3 days following substantial reperfusion of the tissue. For example, the compounds of Formula I could conveniently be administered to a patient with a coronary thrombosis concurrently with the administration of a clot dissolving agent such as streptokinase or urokinase. Administration of compounds of Formula I prior to an ischemia may be indicated in certain instances such as where a patient has substantial risk of heart attack or stroke and would continue until the risk of an ischemic event has substantially disappeared, for example, where the patient has recently suffered a heart attack or stroke, or where the patient is to undergo a surgical procedure requiring a temporary, surgically-induced organ ischemia such as in open heart surgery or coronary by-pass surgery.

The amount of the active ingredient to be administered in the treatment of ischemia can vary widely according to such considerations as the particular compound and dosage unit employed, the mode of administration, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 30 mg/kg. A unit dosage may contain from 25 mg to 525 mg of active ingredient, and can be taken one or more times per day. The active compound of formula 1 can be administered with a pharmaceutical carrier using conventional dosage unit forms either orally, parenterally, topically, or the like, as described below.

The utility of the compounds of Formula I as cardiotonic agents may be determined by administering the test compound (0.1-100 mg/kg) intravenously, intraperitoneally, intraduodenally, or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% heparin-sodium to record arterial blood pressure and administer compounds, respectively. The chest is opened by splitting the sterum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left ventricle of the heart to record left atrial pressure or left ventricular pressure. Heart failure is induced by administering sodium pentobarbital (20 to 40 mg/kg) followed by a continuous infusion of 0.25–2 mg/kg/min. or propranolol hydrochloride (4 mg/kg) followed by a continuous infusion of 0.18 mg/kg/min. to the blood perfusing the heart. Following administration of either of the cardiac depressants, the right atrial pressure dramatically increases and cardiac output is severly depressed. Reversal of these effects by the test compound indicates cardiotonic activity.

The amount of the active ingredient to be administered to the patient for the treatment of cardiotonia can vary widely according to such considerations as the particular compound and dosage unit employed, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 20 mg/kg. A unit dosage may contain from 25 mg to 500 mg of active ingredient, and can be taken one or more times per day. The compounds of Formula I can be administered with a pharmaceutical carrier using conventional dosage unit forms either orally, parenterally, topically, or the like, as described below.

The compounds of this invention can be utilized to achieve the desired pharmacological effect by administration to a patient in need thereof in an appropriately formulated pharmaceutical composition. Therefore, the present invention includes pharmaceutical compositions which are comprised of a pharmaceutically-acceptable carrier and a pharmaceutically-effective amount of a compound of Formula I. A pharmaceutically-effective amount of compound is that amount which produces a result or exerts an influence on the particular condition being treated. The compounds of Formula I can be administered with a pharmaceutical carrier using conventional dosage unit forms either orally, parenternally, topically, or the like. A patient, for the purposes of this invention, is a mammal, including humans, in need of treatment for a particular condition, injury, or disease.

For oral administration the compounds can be formulated into solid or liquid preparations such as capsules, pills, tablets, troches, lozenges, melts, powders, solutions, suspensions, or emulsions and may be prepared according to any method known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment, the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent. The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monoleate.

The suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin or cetyl alcohol. The sterile injectable preparation may also be a sterile injectable solution or suspension in a non-toxic parenterally-acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

For topical use, a cream, ointment, jelly, solution, suspension, or the like, which contains a composition of this invention, can be employed.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

For administration, the compositions of the invention can also contain other conventional pharmaceutically acceptable compounding ingredients as necessary or desired. For example, the compositions may include such ingredients generally referred to as carriers or diluents. These compositions may also be preserved by the addition of an antioxidant such as ascorbic acid or other suitable preservative.

Conventional procedures for preparing such compositions in appropriate dosage forms can be utilized. Whatever the dosage form, it will contain a pharmaceutically effective amount of the compound of this invention.

It should be apparent to one of ordinary skill in the art that changes and modifications can be made to this invention without departing from the spirit or scope of the invention as it is set forth herein.

What is claimed as new and useful is:

1. A process for preparing a compound of the formula

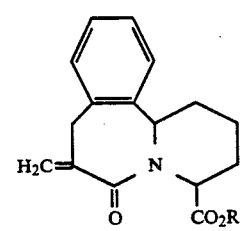

(A)

wherein R is hydrogen, $C_1$-$C_6$ lower alkyl, or ($C_6$-$C_{12}$)aryl($C_1$-$C_6$)lower alkyl, which comprises reacting a compound of the formula wherein R is as defined above with an alkylnitrite of the formula R"ON=, wherein R" is isoamyl or n-propyl, in the presence of acetic acid and an inert solvent under reflux conditions, to produce an intermediate compound of the formula

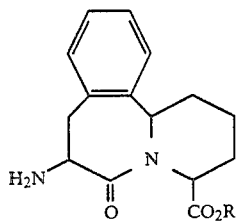
(B)

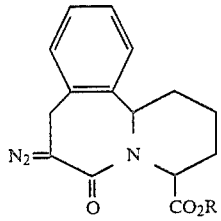
(C)

and sequentially treating C first with strong acid and a phosphine selected from the group consisting of tributylphosphine or triphenylphosphine, at a temperature of about −70° C. to about 50° C., and then with a strong base and formaldehyde to produce the compound of Formula A.

2. A process according to claim 1 wherein R" is n-propyl.

3. A process according to claim 1 wherein the inert solvent is dichloromethane.

4. A process according to claim 1 wherein the strong acid is trifluromethanesulfonic acid.

5. A process according to claim 1 wherein the phosphine is triphenylphosphine.

6. A process according to claim 1 wherein the temperature is −20° C. to −40° C.

7. A process according to claim 1 wherein the strong base is potassium carbonate.

8. A procses according to claim 1 wherein R" is n-propyl, the inert solvent is dichloromethane, the strong acid is trifluoromethanesulfonic acid, the phosphine is tripheylphosphine, the temperature is −20° C. to −40° C., and the strong base is potassium carbonate.

* * * * *